United States Patent
Midgett et al.

(10) Patent No.: US 11,850,432 B2
(45) Date of Patent: Dec. 26, 2023

(54) IMPLANTABLE MEDICAL DEVICE FOR STIMULATING A HUMAN OR ANIMAL HEART

(71) Applicant: BIOTRONIK SE & Co. KG, Berlin (DE)

(72) Inventors: Madeline Anne Midgett, Portland, OR (US); Burkhard Huegerich, Portland, OR (US); R. Hollis Whittington, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/797,165

(22) PCT Filed: Jan. 8, 2021

(86) PCT No.: PCT/EP2021/050286
§ 371 (c)(1),
(2) Date: Aug. 3, 2022

(87) PCT Pub. No.: WO2021/156012
PCT Pub. Date: Aug. 12, 2021

(65) Prior Publication Data
US 2023/0056756 A1    Feb. 23, 2023

Related U.S. Application Data

(60) Provisional application No. 62/969,179, filed on Feb. 3, 2020.

(30) Foreign Application Priority Data

Feb. 18, 2020    (EP) .................................... 20158056

(51) Int. Cl.
*A61N 1/37*        (2006.01)

(52) U.S. Cl.
CPC .................................. *A61N 1/3712* (2013.01)

(58) Field of Classification Search
None
See application file for complete search history.

(56) References Cited

U.S. PATENT DOCUMENTS

| 7,035,687 B1 | 4/2006 | Levine et al. |
| 2005/0159785 A1 | 7/2005 | Rueter |

(Continued)

FOREIGN PATENT DOCUMENTS

| EP | 1136098 A2 | 9/2001 |
| WO | 2017139197 A1 | 8/2017 |

OTHER PUBLICATIONS

International Search Report (PCT/ISA/210) and Written Opinion (PCT/ISA/237) dated May 4, 2021, by the European Patent Office as the International Searching Authority for International Application No. PCT/EP2021/050286. (11 pages).

*Primary Examiner* — Catherine M Voorhees
*Assistant Examiner* — Elizabeth K So
(74) *Attorney, Agent, or Firm* — Buchanan Ingersoll & Rooney PC

(57) ABSTRACT

An implantable medical device for stimulating a heart, comprising a control unit, a memory unit, a stimulation unit for stimulating a cardiac region of a heart, and a detection unit for detecting an electrical signal of the heart. The memory unit comprises a computer-readable program that causes the control unit to perform the following steps: a) detecting capture thresholds during an observation period, each capture threshold detected in response to a sequence of pacing pulses delivered by the stimulation unit; b) storing the detected capture thresholds in the memory unit; c) determining threshold-to-threshold differences between two consecutive capture thresholds; and d) if a maximum determined threshold-to-threshold difference within the observa- (Continued)

tion period is equal to or greater than a predetermined limit, adjusting a pacing output of the stimulation unit based on the maximum capture threshold determined within a first time period which is equal to or shorter than the observation period.

9 Claims, 3 Drawing Sheets

(56) References Cited

U.S. PATENT DOCUMENTS

| | | |
|---|---|---|
| 2007/0021793 A1 | 1/2007 | Voegele et al. |
| 2014/0350623 A1 | 11/2014 | Fischer et al. |
| 2016/0346552 A1 | 12/2016 | Ternes et al. |
| 2018/0036547 A1 | 2/2018 | Reddy |

IMPLANTABLE MEDICAL DEVICE FOR STIMULATING A HUMAN OR ANIMAL HEART

CROSS-REFERENCE TO RELATED APPLICATIONS

This application is the United States National Phase under 35 U.S.C. § 371 of PCT International Patent Application No. PCT/EP2021/050286, filed on Jan. 8, 2021, which claims the benefit of European Patent Application No. 20158056.0, filed on Feb. 18, 2020, and U.S. Provisional Patent Application No. 62/969,179, filed on Feb. 3, 2020, the disclosures of which are hereby incorporated by reference herein in their entireties.

TECHNICAL FIELD

The present invention relates to an implantable medical device according to the preamble of claim 1, to a method for controlling the operation of such an implantable medical device according to the preamble of claim 10, to a computer program product according to the preamble of claim 11 and to another implantable medical device according to the preamble of claim 13.

BACKGROUND

Implantable medical devices for stimulating a human or animal heart, such as cardiac pacemakers, typically employ a capture control feature for assessing ventricular capture. Capture can be described as ventricular stimulation success; it is defined as ventricular cardiac activity in response to an external or artificial stimulation (e.g., by pacemaker).

Capture control features typically use an algorithm to calculate the pacing output necessary to reliably achieve capture while limiting the pacing output to minimize power consumption of the implantable medical device. The capture control feature periodically measures the capture threshold and automatically adjusts the pacing output with the following basic calculation: previous threshold+safety margin=pacing output.

Often, capture control is performed once a day, wherein the applied pacing output is decreased during a capture test to determine the capture threshold. Starting with a pacing output having a high amplitude, the amplitude of the pacing output is iteratively decreased to determine the lowest amplitude at which a ventricular activity still can be captured.

Traditional safety margin algorithms add a fixed margin to either the last measured threshold or the maximum threshold over an evaluation period. These methods typically result in a comparatively higher pacing output and therefore require a comparatively higher power consumption.

International Publication No. 2017/139197 describes a capture management method by which the difference between the minimum and the maximum threshold of a plurality of lastly determined thresholds in a rolling time window is calculated. The higher the determined difference, the higher is the safety margin added to the determined capture threshold in order to determine the pacing output to be used. Thus, this method makes use of a variable safety margin that is added to the highest capture threshold determined in a rolling time window, wherein the margin is high if the variance of the determined capture thresholds is high, and wherein the safety margin is low if the variance of the determined capture thresholds is low.

U.S. Publication No. 2014/0350623 describes a method to identify candidate pulse widths corresponding to a lowest pulse energy sufficient to achieve capture within cardiac tissue of a patient. In this context, the application of different safety margins is also described.

U.S. Publication No. 2016/0346552 and U.S. Publication No. 2018/0036547 exemplarily describe the application of threshold tests and the application of safety margins to the determined capture threshold in order to determine the pacing output (stimulation amplitude).

The present disclosure is directed toward overcoming one or more of the above-mentioned problems, though not necessarily limited to embodiments that do.

SUMMARY

It is an object of the present invention to provide an implantable medical device for stimulating a human or animal heart, wherein the device has a lower power consumption than implantable devices known from prior art but still guarantees high patient safety with respect to cardiac capture.

At least this object is achieved with an implantable medical device having the features of claim 1. Such an implantable medical device is intended for stimulating a human or animal heart. It comprises a control unit, a memory unit, a stimulation unit for stimulating a cardiac region of the human or animal heart, and a detection unit for detecting an electrical signal of the same heart. In this context, the detection unit typically detects a ventricular signal of the heart. The stimulation unit may stimulate an atrium or a ventricle of the human or animal heart. Often, the stimulation unit is intended to stimulate the right ventricle of the patient's heart.

According to the presently claimed invention, the memory unit comprises a computer-readable program that causes the control unit to perform the steps explained below when being executed on the control unit.

In a first step, capture thresholds are detected with the detection unit. This detection is done during an observation period. In this context, each capture threshold is detected in response to a sequence of pacing pulses delivered by the stimulation unit. Thus, the detection unit detects a cardiac activity in response to an external or artificial stimulus.

The detected capture thresholds are stored in the memory unit. Typically, a time information is stored together with the capture thresholds. Then, it can be easily seen at which time point a specific capture threshold has been detected.

A threshold difference is determined between each pair of two consecutive capture thresholds. For such determination, at least two capture thresholds are necessary. If a first capture threshold and a second capture threshold have been detected, the threshold-to-threshold difference between the first capture threshold and the second capture threshold can be calculated. If afterwards a third capture threshold is determined, a threshold-to-threshold difference between the second capture threshold and the third capture threshold can be calculated. To give an example, in case of 30 capture thresholds, 29 threshold-to-threshold differences between two consecutive capture thresholds in each case will result.

The calculated threshold-to-threshold differences are then further evaluated. For this purpose, a maximum threshold-to-threshold difference determined within the observation period is identified. If this maximum threshold-to-threshold difference is equal to or greater than a predetermined limit, this indicates that the inter-threshold variety is rather high. Then, a higher pacing output is necessary to safely guarantee ventricular capture. Therefore, the pacing output of the stimulation unit is, in this alternative, adjusted on the basis of the maximum capture threshold determined within a first time period. In this context, the first time period is equal to or shorter than the observation period.

If, on the other hand, the maximum determined threshold-to-threshold difference within the observation period is smaller than the predetermined limit, this indicates that the inter-threshold variance of the individual thresholds is comparatively low. Then, it can also be guaranteed to achieve cardiac capture when only relying on the maximum amplitude from a shorter time period than the first time period. Therefore, the pacing output of the stimulation unit is, in this alternative, adjusted on the basis of the maximum capture threshold determined within a second time period, wherein the second time period is shorter than the first time period.

It should be understood that the first time period and the second time period extend from the time point of adjusting the pacing output of the stimulation unit to the past. Thus, the first time period covers more capture thresholds and therefore more threshold-to-threshold differences than the second time period, wherein both the first time period and the second time period cover the most recent threshold-to-threshold differences prior to the adjustment of the pacing output of the stimulation unit.

This dynamic aspect of the algorithm employed by the computer-readable program offers a power savings opportunity considering the power and safety trade-off that comes with the length of the maximum threshold evaluation period, i.e., the first time period or the second time period. Lengthening the evaluation period that tracks the maximum measured capture threshold significantly raises the residing overall average pace output amplitude. However, the dynamic performance lowers the overall average pace output amplitude during periods of capture threshold stability by shortening this maximum capture threshold evaluation period to the second time period.

The first time period and the second time period are rolling window time periods that always ends at the time at which the pacing output of the stimulation unit is adjusted by the method employed by the computer-readable program. Thus, the endpoint of the time period always moves forward in time. Likewise, the starting point of the respective time period also moves forward in time if the time period itself is not lengthened. Thus, the presently claimed implantable medical device is a device that supports capture threshold processing including capture threshold storing using a rolling window, maximum threshold measurement and threshold-to-threshold variation measurement.

In an embodiment, the implantable medical device is an intra-cardiac device. The device is capable of delivering stimulation to cardiac tissue and measuring the capture threshold of cardiac capture or ventricular capture, respectively.

In contrast to prior art solutions, the method employed by the presently claimed implantable medical device uses a novel measure of threshold stability to determine how long of a capture threshold evaluation period should be tracked to measure a patient's maximum capture threshold and determine the pacing output based on this maximum capture threshold. This allows a faster dynamic response during periods of stable capture threshold which reduces overall pacing output, while maintaining safety through a long window during periods of capture threshold instability.

In an embodiment, the capture threshold progress is evaluated. In this embodiment, the stored capture thresholds are, e.g., used to evaluate whether there is a risk of an undesired disassociation of the implantable medical device from cardiac tissue. If a continuous increase of the capture threshold is detected, this might indicate that the implantable medical device is about to disassociate from cardiac tissue. In such a case, immediate counteractions can be taken to guarantee safe implantation of the implantable medical device at its intended site of implantation. Thus, patient safety is increased in this embodiment. If the capture threshold first increases and afterwards decreases to increase and decrease again, this can be seen as indication that there is no disassociation of the implantable medical device from its implantation site, but rather reflects natural fluctuations of the capture threshold.

In an embodiment, the step of detecting capture thresholds with the detection unit is performed once a day. For this purpose, typically a plurality of measurements is necessary during which the pacing output used for stimulating the cardiac tissue is lowered in an iterative way. The capture threshold is the last value of the pacing output at which capture can be determined, wherein the first pacing output at which no cardiac capture can be detected falls below the capture threshold.

In an embodiment, the computer-readable program causes the control unit to determine the pacing output by adding a safety margin to the maximum capture threshold on the basis of which the pacing output is to be adjusted. Such a safety margin guarantees cardiac capture even if small other variances of the capture threshold are present. Thus, such a safety margin enhances patient safety even if it consumes somewhat more energy than working without safety margin. Expressed in other words, the safety margin securely ensures that cardiac capture will occur by stimulation with a pacing output that results from adding the safety margin to the previously determined maximum capture threshold of the first time period or the second time period.

In an embodiment, the computer-readable program causes the control unit to set the safety margin independently on the determined threshold-to-threshold differences and, alternatively or additionally, independently on the determined maximum capture threshold. Thus, in contrast to prior art solutions which rely on a variation of the safety margin to be applied to a specific maximum capture threshold for determining the final pacing output, this embodiment of the presently claimed invention does not vary the safety margin, but rather relies on a skilled choice of the maximum threshold to be applied for calculating the pacing output. As already outlined above, the presently claimed approach reflects much better the physiological needs of a patient, the heart of whom is stimulated by the implantable medical device, while saving at the same time a significant amount of energy necessary for pacing the patient's heart. The approach taken by the presently described invention does not require a variable safety margin. Rather, the safety margin can be kept constant over the entire lifetime of the implantable medical device or at least over almost the entire lifetime of the implantable medical device.

In an embodiment, the computer-readable program causes the control unit to set the safety margin during a third time period higher than after the third time period. In this context, the third time period is a time period directly after implantation of the implantable medical device. This embodiment considers that the capture threshold is typically somewhat higher and more variable during the first weeks after implantation and then typically decreases to a lower relatively constant value. Thus, when combining the previous and the instant embodiments with each other, the safety margin is varied only during the very first time after implantation to be then kept constant for the remaining lifetime of the implantable medical device. This can be considered as a constant safety margin over almost the entire lifetime of the implantable medical device. In an embodiment, the term "almost the entire lifetime of the implantable medical device" is to be construed as meaning the entire lifetime minus the third time period (irrespective of any variations of the safety margin within the third time period).

In an embodiment, the third time period is a time period covering 1 day to 200 days, in particular 5 days to 190 days, in particular 10 days to 180 days, in particular 20 days to 170 days, in particular 30 days to 160 days, in particular 40 days to 150 days, in particular 50 days to 140 days, in particular 60 days to 130 days, in particular 70 days to 120 days, in particular 80 days to 110 days, in particular 90 days to 100 days. In any case, the third time period starts immediately with implantation of the implantable medical device, in particular with implantation of the implantable medical device into the patient's heart.

In an embodiment, the implantable medical device is a leadless peacemaker. Leadless pacemakers are implanted into the patient's heart, i.e., they can also be denoted as intra-cardiac devices. Leadless pacemakers are typically smaller than conventional pacemakers and thus offer less space for energy sources like batteries. Therefore, the power consumption of leadless pacemakers is to be even better controlled than the power consumption of conventional pacemakers. Therefore, leadless pacemakers are a very interesting field of application of the presently claimed invention since the presently claimed invention will significantly extend the lifetime of leadless pacemakers and can thus make such devices even more attractive than they already are.

In an embodiment, the computer-readable program causes the control unit to decrease the voltage of the pacing output at most by a predetermined maximum value each day. If this embodiment is applied, an initial voltage of the pacing output is more limited than potentially possible according to the determined capture thresholds and threshold-to-threshold differences. Therefore, an operation of the implantable medical device by this embodiment results in a higher energy consumption than absolutely necessary. However, it further increases patient safety. Furthermore, the predetermined maximum value by which the voltage of the pacing output can be at most decreased each day can be set such that the time period during which the energy consumption of the implantable medical device is higher than necessarily needed is limited to a few days or a few weeks. In doing so, it is possible to set the pacing output to a higher level in an initial time period of operation of the implantable medical device, e.g., directly after implantation. To give a further example, the limited decrease of the voltage of the pacing output can be employed during the third period of time. Then, a sufficiently high pacing output to achieve cardiac capture can be guaranteed even though the cardiac tissue of the patient might not have yet achieved its final susceptibility with respect to a stimulation by a pacing pulse.

In an embodiment, the predetermined maximum value of the step down size lies in a range between 0.05 V and 0.2 V, in particular between 0.075 V and 0.15 V, in particular between 0.1 V and 0.12 V.

In an embodiment, the observation period and/or the first time period are a time period covering 7 days to 50 days, in particular 10 days to 45 days, in particular 15 days to 40 days, in particular 20 days to 35 days, in particular 25 days to 30 days. In an embodiment, the first time period has the same length as the observation period, i.e., the first time period equals the observation period. To give an example, the observation period might cover 30 days. Then, the first time period would cover the last 30 days prior to the day on which the pacing output of the stimulation unit is adjusted according to the method employed by the presently claimed implantable medical device.

In an embodiment, the second time period is a time period covering 2 days to 14 days, in particular 3 days to 13 days, in particular 4 days to 12 days, in particular 5 days to 11 days, in particular 6 days to 10 days, in particular 7 days to 9 days. A particular appropriate second time period is a time period of 2 days to 6 days, e.g., 3 days, 4 days, 5 days or 6 days.

An aspect of the present invention relates to a method for controlling the operation of an implantable medical device for stimulating a human or animal heart according to the preceding explanations. This method comprises the steps explained in the following.

First, an electrical signal of a human or animal heart is detected with a detection unit. This detection serves for detecting capture thresholds during an observation period. Each capture threshold is detected in response to a sequence of pacing pulses delivered by a stimulation unit for stimulating a cardiac region of the same heart.

The detected capture thresholds are stored in the memory unit of the implantable medical device.

Furthermore, threshold-to-threshold differences between two consecutive capture thresholds in each case are determined.

Afterwards, it is decided if a maximum determined threshold-to-threshold difference within the observation time period is equal to or greater than a predetermined limit (first alternative) or lower than the predetermined limit (second alternative). In case of the first alternative, a pacing output of the stimulation unit is adjusted on the basis of the maximum capture threshold determined within a first time period. In this context, the first time period is equal to or shorter than the observation period. In case of the second alternative, the pacing output of the stimulation unit is adjusted on the basis of the maximum capture threshold determined within a second time period. In this context, the second time period is shorter than the first time period. The first time period and the second time period are time periods reaching from the time point of adjusting the pacing output of the stimulation unit to the past.

An aspect of the present invention relates to a computer program product comprising computer-readable code that causes a control unit to perform the following steps when executed on the control unit.

First, an electrical signal of a human or animal heart is detected with a detection unit. This detection serves for detecting capture thresholds during an observation period. Each capture threshold is detected in response to a sequence of pacing pulses delivered by a stimulation unit for stimulating a cardiac region of the same heart.

The detected capture thresholds are stored in the memory unit of an implantable medical device.

Furthermore, threshold-to-threshold differences between two consecutive capture thresholds in each case are determined.

Afterwards, it is decided if a maximum determined threshold-to-threshold difference within the observation time period is equal to or greater than a predetermined limit (first alternative) or lower than the predetermined limit (second alternative). In case of the first alternative, a pacing output of the stimulation unit is adjusted on the basis of the maximum capture threshold determined within a first time period. In this context, the first time period is equal to or shorter than the observation period. In case of the second alternative, the pacing output of the stimulation unit is adjusted on the basis of the maximum capture threshold determined within a second time period. In this context, the second time period is shorter than the first time period. The first time period and the second time period are time periods reaching from the time point of adjusting the pacing output of the stimulation unit to the past.

An aspect of the present invention relates to a medical method of treatment of a human or animal patient in need of such treatment. This treatment takes place by means of an implantable medical device for stimulating a human or animal heart, in particular with an implantable medical device according to the preceding explanations. Such an implantable medical device comprises a control unit, a memory unit, a stimulation unit for stimulating a cardiac region of a human or animal heart and a detection unit for detecting an electrical signal of the same heart. The method comprises the steps explained in the following.

First, an electrical signal of a human or animal heart is detected with the detection unit. This detection serves for detecting capture thresholds during an observation period. Each capture threshold is detected in response to a sequence of pacing pulses delivered by the stimulation unit for stimulating a cardiac region of the same heart.

The detected capture thresholds are stored in the memory unit of the implantable medical device.

Furthermore, threshold-to-threshold differences between two consecutive capture thresholds in each case are determined.

Afterwards, it is decided if a maximum determined threshold-to-threshold difference within the observation time period is equal to or greater than a predetermined limit (first alternative) or lower than the predetermined limit (second alternative). In case of the first alternative, a pacing output of the stimulation unit is adjusted on the basis of the maximum capture threshold determined within a first time period. In this context, the first time period is equal to or shorter than the observation period. In case of the second alternative, the pacing output of the stimulation unit is adjusted on the basis of the maximum capture threshold determined within a second time period. In this context, the second time period is shorter than the first time period. The first time period and the second time period are time periods reaching from the time point of adjusting the pacing output of the stimulation unit to the past.

Afterwards, the human or animal heart is stimulated by applying a pacing pulse by the stimulation unit with the pacing output adjusted in the preceding step. Thus, the pacing pulse can have different amplitudes depending on the previously observed variance of the capture threshold. Typically, the pacing pulse has a higher amplitude (i.e., the stimulation unit is operated with a higher pacing output) if the variance of the detected threshold-to-threshold differences was comparatively high. In contrast, the pacing pulse will have a lower amplitude (i.e., the stimulation unit is operated with a lower pacing output) in case that lower variances between the individual capture thresholds have been determined, i.e., if the threshold-to-threshold differences were comparatively lower.

A further aspect of the present invention is another implantable medical device for stimulating human or animal heart that can be combined with any of the preceding explained embodiments but that is also claimed independent on the preceding explained aspects and embodiments. This further implantable medical device comprises a control unit, a memory unit, a stimulation unit for stimulating a cardiac region of a human or animal heart, and a detection unit for detecting an electrical signal of the same heart.

The memory unit comprises a computer-readable program that causes the control unit to perform the steps explained in the following when executed on the control unit.

First, capture thresholds are detected with the detection unit during an observation period. In this context, each capture threshold is detected in response to a sequence of pacing pulses delivered by the stimulation unit.

The detected capture thresholds are stored in the memory unit.

A voltage of the pacing output of the stimulation unit is decreased at most by a predetermined maximum value each day. In this context, the voltage of the pacing output remains at least as high as a maximum capture threshold determined within a time period being equal to or shorter than the observation period. According to an embodiment, the voltage of the pacing output remains at least as high as a maximum capture threshold determined within a time period being equal to or shorter than the observation period with an added safety margin. In doing so, it is guaranteed that the applied voltage of the pacing output is always at least as high as the determined capture threshold with an added safety margin, but at the same time is reduced only in small steps from the previous value. This helps to address sudden decreases in capture threshold that may only be temporary. According to an embodiment of the present invention, there is a predetermined value defined which represents the maximum value for a variation of the pacing output, especially for one decrease of the pacing output.

In an embodiment, the limited decrease of the voltage of the pacing output is performed only over a predetermined period of time, e.g., during the third time period as defined above.

In an embodiment, the predetermined maximum value lies in a range between 0.05 V and 0.2 V, in particular between 0.075 V and 0.15 V, in particular between 0.1 V and 0.12 V.

In an embodiment, the implantable medical device does not only implement a limited decrease of the initial voltage of the pacing output, but also an adjustment of the pacing output in response to observed capture threshold variances. In this embodiment, the computer-readable program causes the control unit to adjust the pacing output of the stimulation unit either according to a first alternative or according to a second alternative. According to the first alternative, the pacing output is adjusted on the basis of the maximum capture threshold determined within a first time period, if a maximum determined threshold-to-threshold difference within the observation period is equal to or greater than a predetermined limit. In this context, the first time period is equal to or shorter than the observation period. According to the second alternative, the pacing output of the stimulation unit is adjusted on the basis of the maximum capture threshold determined within a second time period, if the maximum determined threshold-to-threshold difference within the observation period is smaller than the predetermined limit. In this context, the second time period is shorter than the first time period.

Thus, in this embodiment, the voltage of the pacing output is decreased each day by the predetermined maximum value until it reaches the output of the algorithm evaluating the capture threshold variances in the past. Instances of non-capture are reliably avoided by this operational mode. If, however, the output of the algorithm evaluating the capture threshold variances in the past results in a higher necessary capture threshold than the voltage of the last pacing output minus the maximum value by which the voltage of the pacing output has been decreased so far at most each day, the pacing output is immediately updated to the pacing output determined on the basis of the maximum capture threshold determined by the algorithm.

An aspect of the present invention relates to a method for controlling the operation of an implantable medical device for stimulating a human or animal heart, the method comprising the following steps: a) detecting, with a detection unit for detecting an electrical signal of a human or animal heart, capture thresholds during an observation period, each capture threshold being detected in response to at least one pacing pulse or a sequence of pacing pulses delivered by a stimulation unit for stimulating a cardiac region of the same heart; b) storing the detected capture thresholds in a memory unit of the implantable medical device; c) decreasing a voltage of a pacing output of the stimulation unit at most by a predetermined maximum value each day, wherein the voltage of the pacing output remains at least as high as a maximum capture threshold determined within a time period being equal to or shorter than the observation period. According to an embodiment, the voltage of the pacing output remains at least as high as a maximum capture threshold determined within a time period being equal to or shorter than the observation period with an added safety margin.

An aspect of the present invention relates to a computer program product comprising computer-readable code that causes a control unit to perform the following steps when executed on the control unit: a) detecting, with a detection unit of an implantable medical device for stimulating a human or animal heart, the detection unit being configured to detect an electrical signal of a human or animal heart, capture thresholds during an observation period, each capture threshold being detected in response to a pacing pulse delivered by a stimulation unit of the implantable medical device, the stimulation unit being configured to stimulate a cardiac region of the same heart; b) storing the detected capture thresholds in a memory unit of the implantable medical device; c) decreasing a voltage of a pacing output of the stimulation unit at most by a predetermined maximum value each day, wherein the voltage of the pacing output remains at least as high as a maximum capture threshold determined within a time period being equal to or shorter than the observation period. According to an embodiment, the voltage of the pacing output remains at least as high as a maximum capture threshold determined within a time period being equal to or shorter than the observation period with an added safety margin.

An aspect of the present invention relates to a method of treatment of a human or animal patient in need of such treatment by means of an implantable medical device for stimulating a human or animal heart, wherein the implantable medical device comprises a control unit, a memory unit, a stimulation unit for stimulating a cardiac region of a human or animal heart, and a detection unit for detecting an electrical signal of the same heart, the method comprising the following steps: a) detecting, with the detection unit, capture thresholds during an observation period, each capture threshold being detected in response to a pacing pulse de-livered by the stimulation unit; b) storing the detected capture thresholds in the memory unit; c) decreasing a voltage of a pacing output of the stimulation unit at most by a predetermined maximum value each day, wherein the voltage of the pacing output remains at least as high as a maximum capture threshold determined within a time period being equal to or shorter than the observation period with an added safety margin; d) stimulating the human or animal heart by applying a pacing pulse with the pacing output adjusted in the preceding step.

An aspect of the present invention relates to a method for controlling the operation of an implantable medical device for stimulating a human or animal heart, the method comprising the following steps: a) detecting, with a detection unit for detecting an electrical signal of a human or animal heart, capture thresholds during an observation period, each capture threshold being detected in response to at least one pacing pulse delivered by a stimulation unit for stimulating a cardiac region of the same heart; b) storing the detected capture thresholds in a memory unit of the implantable medical device; c) determining threshold-to-threshold differences between two consecutive capture thresholds in each case; and d) if a maximum determined threshold-to-threshold difference within the observation period is equal to or greater than a predetermined limit, adjusting a pacing output of the stimulation unit on the basis of the maximum capture threshold determined within a first time period, the first time period being equal to or shorter than the observation period; or if the maximum determined threshold-to-threshold difference within the observation period is smaller than the predetermined limit, adjusting the pacing output of the stimulation unit on the basis of the maximum capture threshold determined within a second time period, the second time period being shorter than the first time period.

An aspect of the present invention relates to a method of treatment of a human or animal patient in need of such treatment by means of an implantable medical device for stimulating a human or animal heart, wherein the implantable medical device comprises a control unit, a memory unit, a stimulation unit for stimulating a cardiac region of a human or animal heart, and a detection unit for detecting an electrical signal of the same heart, the method comprising the following steps: a) detecting, with the detection unit, capture thresholds during an observation period, each capture threshold being detected in response to a pacing pulse delivered by the stimulation unit; b) storing the detected capture thresholds in the memory unit; c) determining threshold-to-threshold differences between two consecutive thresholds in each case; d) if a maximum determined threshold-to-threshold difference within the observation period is equal to or greater than a predetermined limit, adjusting a pacing output of the stimulation unit on the basis of the maximum capture threshold determined within a first time period, the first time period being equal to or shorter than the observation period; or if the maximum determined threshold-to-threshold difference within the observation period is smaller than the predetermined limit, adjusting the pacing output of the stimulation unit on the basis of the maximum capture threshold determined within a second time period, the second time period being shorter than the first time period; and e) stimulating the human or animal heart by applying a pacing pulse with the pacing output adjusted in the preceding step.

All embodiments of the individual implantable medical devices described herein can be combined in any desired way and can be transferred to the respective other implantable medical device, to the described methods and to the described computer program products. Furthermore, any embodiments of the described methods can be combined in any desired way and can be transferred to the respective other methods, to the different implantable medical devices and to the computer program products. Finally, any embodiments of the computer program products can be combined in any desired way and can be transferred in any combination to the respective other computer program products, to the described implantable medical devices, and to the described methods.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further details of aspects of the present invention will be explained with respect to exemplary embodiments and accompanying Figures. In the Figures.

DETAILED DESCRIPTION

Figure 1:
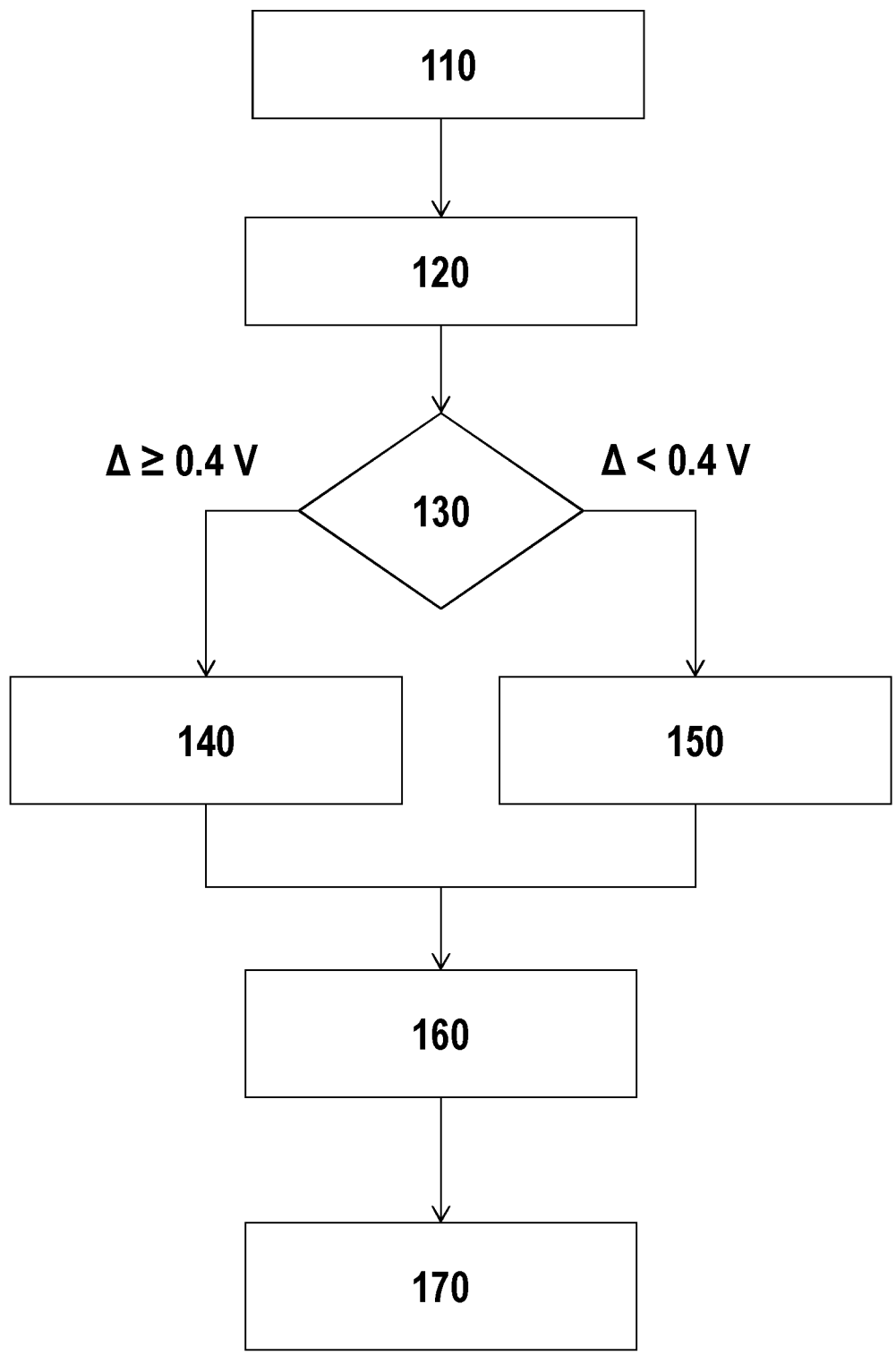
FIG. 1 shows a schematic workflow of a first embodiment of a method for determining a pacing output of a stimulation unit of an implantable medical device.

FIG. 1 illustrates the workflow of a method implemented by a cardiac pacemaker as implantable medical device. First, a detection unit of the cardiac pacemaker serves for detecting 110 capture thresholds during an observation period. Afterwards, a determination 120 of threshold-to-threshold differences between two consecutive capture thresholds is carried out.

Then, a decision 130 takes place whether the maximum threshold-to-threshold difference determined within the observation period is either equal to or above a preset limit or below this limit. Thereby, the limit is set to be 0.4 V in the embodiment of FIG. 1. If the maximum determined threshold-to-threshold difference is at least 0.4 V, a selection 140 of the maximum capture threshold during the past 30 days takes place. In this context, 30 days serve as first time period. If, on the other hand, the maximum determined threshold-to-threshold difference is below 0.4 V, a selection 150 of the maximum determined capture threshold during the past 3 days takes place. In this context, 3 days serve as second time period. Afterwards, an addition 160 of a safety margin to the selected maximum capture threshold is carried out.

Finally, an adjustment 170 of a pacing output for a pacing pulse by a stimulation unit of the implantable medical device is performed. This adjustment is based on the selected maximum capture threshold and defines the pacing output to be the sum of the selected capture threshold and the safety margin.

This method is typically applied once a day by the cardiac pacemaker.

The safety margin added to the selected maximum capture threshold in step 160 is chosen to be 0.4 V in case that the cardiac pacemaker has been implanted no longer than a predefined period since implant and is reduced to 0.3 V in case that the implantation of the cardiac pacemaker has been carried out longer than the predefined time period. According to an embodiment, the predefined period is 20 to 150 days, or 50 to 120 days, or 70 to 120 days, or 90 to 120 days, or 100 to 120 days, or 112 days.

Figure 2:
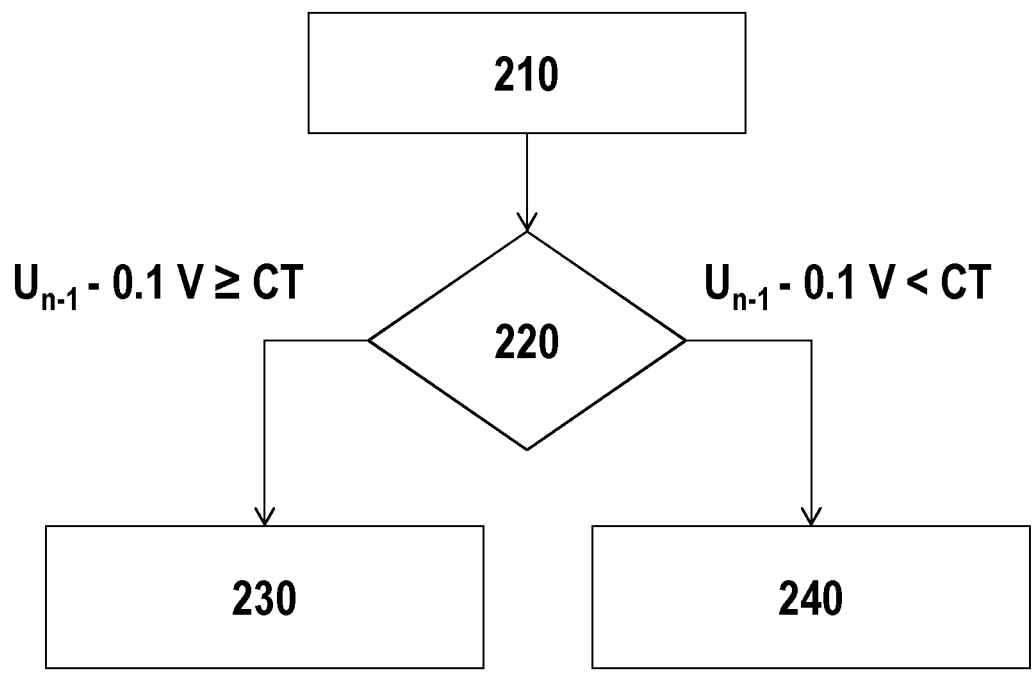
FIG. 2 shows a schematic workflow of a second embodiment of a method for determining a pacing output of a stimulation unit of an implantable medical device.

FIG. 2 shows a schematic workflow of a further method that is applied by another cardiac pacemaker, serving as further embodiment of an implantable medical device.

First, a determination 210 of capture thresholds takes place during an observation period. This detection is carried out with a detection unit of the cardiac pacemaker. Each capture threshold is determined in response to a sequence of pacing pulses delivered by a stimulation unit of the cardiac pacemaker.

The capture thresholds generally serve for adjusting a pacing output of the cardiac pacemaker. However, prior to adjusting the pacing output, a determination 220 takes place regarding a decrease of the previously applied pacing output. If a voltage U of the previously applied pacing output reduced by 0.1 V is at least as high as the determined capture threshold CT (optionally plus a safety margin), an adjustment 230 of the pacing output to the previously applied pacing output minus 0.1 V takes place.

If, however, the determination 220 gives the result that the detection 210 of the capture threshold (optionally plus a safety margin) resulted in a higher capture threshold CT than a voltage U of the previously applied pacing output reduced by 0.1 V, an adjustment 240 of the pacing output on the basis of the determined capture threshold takes place (a safety margin is optionally considered and added to the detected maximum capture threshold). According to an embodiment, the pacing output is immediately increased to the output determined by the algorithm.

This method guarantees that the pacing output is reduced in an iterative way by a maximum value which is set to 0.1 V in the present embodiment until the pacing output reaches the algorithm-determined pacing output. This method is performed such that an unforeseeable increase in the necessary capture threshold will automatically lead to an increase of the pacing output so that the safe cardiac capture can always be guaranteed. Furthermore, even if no iterative decrease of a previous pacing output is done, the method guarantees that the applied pacing output never falls below the necessary capture threshold.

The embodiment shown in FIG. 2 can be combined with the embodiment of FIG. 1 or can be implemented without the embodiment of FIG. 1 in a cardiac pacemaker.

Figure 3:
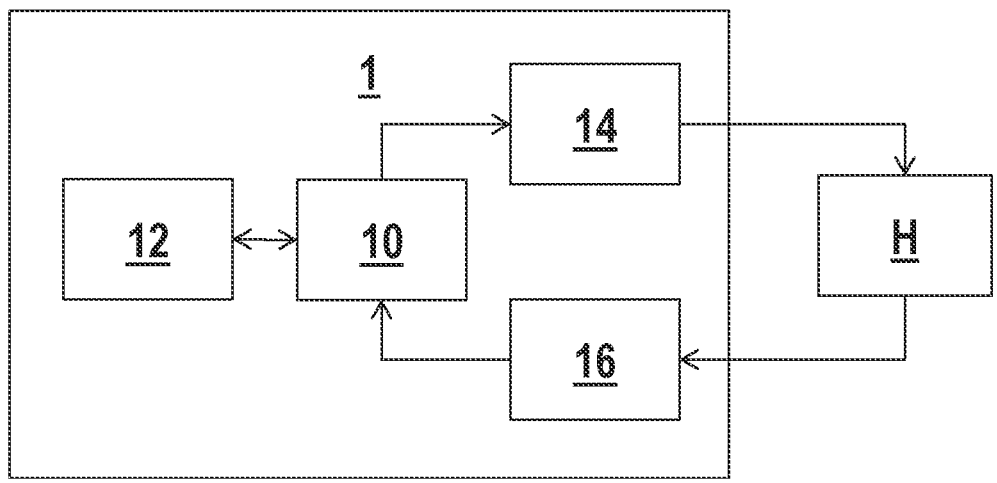
FIG. 3 shows a schematic representation of an implantable medical device of a first embodiment.

FIG. 3 shows a schematic representation of an implantable medical device 1 (e.g., a cardiac pacemaker) for stimulating a human or animal heart H, comprising a control unit 10 (e.g., a processor), a memory unit 12, a stimulation unit 14 for stimulating a cardiac region of a human or animal heart, and a detection unit 16 for detecting an electrical signal of the same heart H. The memory unit 12 comprises a computer-readable program that causes the control unit 10 to perform the steps of the workflow shown in FIG. 1 when executed on the control unit 10.

Figure 4:
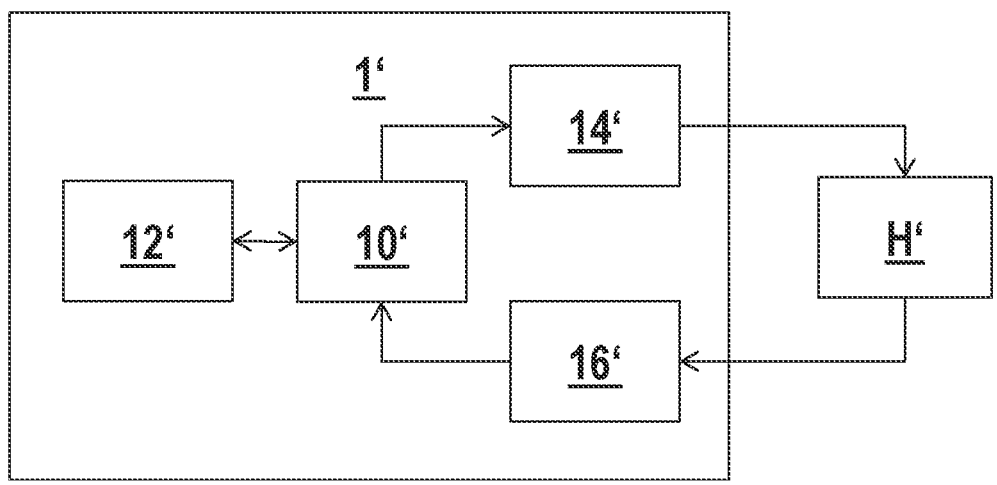
FIG. 4 shows a schematic representation of an implantable medical device of a second embodiment.

FIG. 4 shows a schematic representation of an implantable medical device 1' (e.g., a cardiac pacemaker) for stimulating a human or animal heart H', comprising a control unit 10' (e.g., a processor), a memory unit 12', a stimulation unit 14' for stimulating a cardiac region of a human or animal heart H', and a detection unit 16' for detecting an electrical signal of the same heart H'. The memory unit 12' comprises a computer-readable program that causes the control unit 10' to perform the steps of the workflow shown in FIG. 2 when executed on the control unit 10'

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An implantable medical device for stimulating a human or animal heart, comprising a control unit, a memory unit, a stimulation unit for stimulating a cardiac region of a human or animal heart, and a detection unit for detecting an electrical signal of the same heart, wherein the memory unit comprises a computer-readable program that causes the control unit to perform the following steps when executed on the control unit:
   a) detecting, with the detection unit, capture thresholds during an observation period, each capture threshold being detected in response to a sequence of pacing pulses delivered by the stimulation unit;
   b) storing the detected capture thresholds in the memory unit;
   c) determining threshold-to-threshold differences between two consecutive capture thresholds; and
   d) if a maximum determined threshold-to-threshold difference within the observation period is equal to or greater than a predetermined limit, adjusting a pacing output of the stimulation unit on the basis of the maximum capture threshold determined within a first time period, the first time period being equal to or shorter than the observation period; or if the maximum determined threshold-to-threshold difference within the observation period is smaller than the predetermined limit, adjusting the pacing output of the stimulation unit on the basis of the maximum capture threshold determined within a second time period, the second time period being shorter than the first time period.

2. The implantable medical device according to claim 1, wherein the computer-readable program causes the control unit to determine the pacing output by adding a safety margin to the maximum capture threshold on the basis of which the pacing output is adjusted.

3. The implantable medical device according to claim 2, wherein the computer-readable program causes the control unit to set the safety margin independently on the determined threshold-to-threshold differences.

4. The implantable medical device according to claim 2, wherein the computer-readable program causes the control unit to set the safety margin during a third time period greater than after the third time period, the third time period being a time period starting with implantation of the implantable medical device.

5. The implantable medical device according to claim 1, wherein the implantable medical device is a leadless pacemaker.

6. The implantable medical device according to claim 1, wherein the computer-readable program causes the control unit to decrease a voltage of the pacing output at most by a predetermined maximum value each day.

7. The implantable medical device according to claim 6, wherein the predetermined maximum value lies in a range between 0.05 V and 0.2 V.

8. The implantable medical device according to claim 1, wherein the observation period and/or the first time period are a time period covering 7 days to 50 days.

9. The implantable medical device according to claim 1, wherein the second time period is a time period covering 2 days to 14 days.

* * * * *